(12) United States Patent
Srirama

(10) Patent No.: US 9,852,264 B1
(45) Date of Patent: Dec. 26, 2017

(54) AUTHENTIC AND VERIFIABLE ELECTRONIC WELLNESS RECORD

(71) Applicant: Padmanabaiah Srirama, Glen Allen, VA (US)

(72) Inventor: Padmanabaiah Srirama, Glen Allen, VA (US)

( * ) Notice: Subject to any disclaimer, the term of this patent is extended or adjusted under 35 U.S.C. 154(b) by 235 days.

(21) Appl. No.: 14/697,602

(22) Filed: Apr. 27, 2015

Related U.S. Application Data

(60) Provisional application No. 62/026,998, filed on Jul. 21, 2014.

(51) Int. Cl.
*G06F 3/00* (2006.01)
*G06F 19/00* (2011.01)
*G06F 21/32* (2013.01)

(52) U.S. Cl.
CPC ...... *G06F 19/3418* (2013.01); *G06F 19/3487* (2013.01); *G06F 21/32* (2013.01)

(58) Field of Classification Search
CPC .................................................. G06F 19/3418
USPC ........................................................ 715/700
See application file for complete search history.

(56) References Cited

U.S. PATENT DOCUMENTS

| | | | | |
|---|---|---|---|---|
| 2002/0108000 A1* | 8/2002 | Iori | .................... | G07C 9/00087 710/11 |
| 2003/0176815 A1* | 9/2003 | Baba | .................. | A61B 5/02438 600/595 |
| 2004/0169635 A1* | 9/2004 | Ghassabian | ........... | G06F 1/1613 345/156 |
| 2007/0033069 A1* | 2/2007 | Rao | ........................ | A63B 24/00 705/2 |
| 2015/0074615 A1* | 3/2015 | Han | .................... | G06K 9/00033 715/863 |
| 2015/0082408 A1* | 3/2015 | Yeh | ...................... | G06F 19/3406 726/9 |
| 2015/0238819 A1* | 8/2015 | Volkerink | .......... | A63B 24/0087 482/4 |
| 2015/0269354 A1* | 9/2015 | Klassen | ................. | G06Q 50/01 700/91 |

OTHER PUBLICATIONS

Authors et al, "Auto setting at gym", Sptember Jul. 2006, ip.com.*

* cited by examiner

*Primary Examiner* — Jason C Olson

(57) ABSTRACT

A biometric reading device, for tracking fitness activity, via creating a profile of the user on web portal, comprising a touch screen with the front camera, finger print scanner for thumb, finger print scanner for index finger, and extendable voice recorder at the base panel, the circuit board, essential to be linked with the web portal, a start and stop press button to initiate and stop the fitness tracking record respectively, the speakers at both ends, motion sensors adjacent to both the speakers, audio output, micro USB input to connect pulse measuring or wearable devices, and the power source input. The devise is used for tracking and maintain the fitness activity record, creating the individual profile or account by capturing the biometric data (finger prints, voice recordings and facial image) of the user. The invention provides a method, system and device for monitoring exercise and managing fitness activity across diverse exercise machines with user's profile or account, linked with the web portal system, generating an authenticated fitness report for both, individual users and fitness center users.

2 Claims, 5 Drawing Sheets

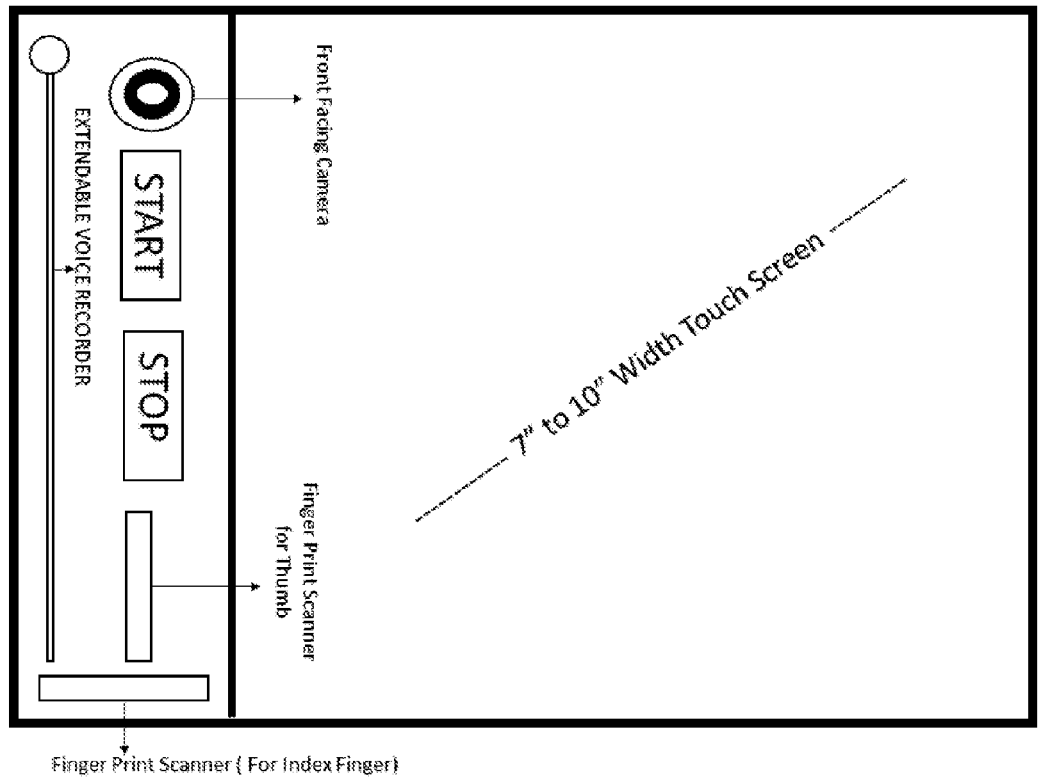
FIG:5
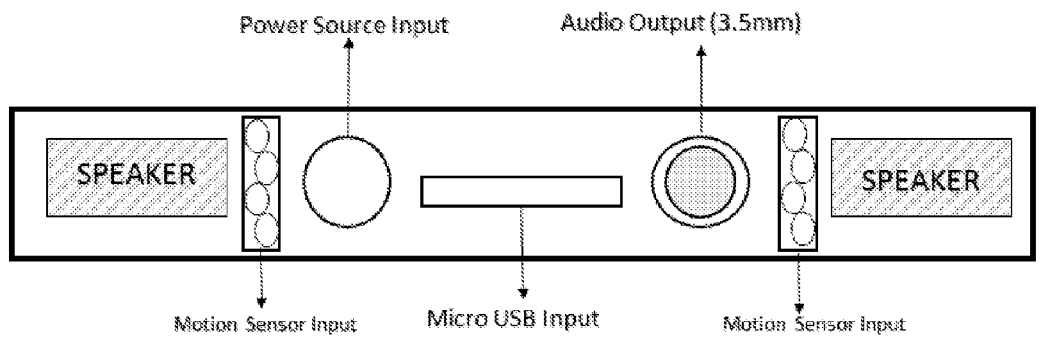
FIG:6

AUTHENTIC AND VERIFIABLE ELECTRONIC WELLNESS RECORD

FIELD OF THE INVENTION

The present invention relates to an apparatus, systems and method for managing fitness data. More specifically, this invention relates to electronically implemented system for and method of recording and analyzing wellness record, both for individual users and for fitness center users.

BACKGROUND OF THE INVENTION

Management of fitness data is performed for a variety of reasons. Many fitness participants who engage in fitness activities such as weight training and aerobic activities often track fitness data such as times, dates, the amount of weight, the number of repetitions, and the number of sets for various exercises, sports, or other activities.

One method of recording the fitness data includes entering the fitness data using a writing instrument into a log book or onto other types of paper media. The fitness data is later accessed by the fitness participant to monitor changes in any of the recorded categories. In order to access the fitness data and draw any conclusions regarding progress, the fitness participant must at least access two records. Often, however, several records must be evaluated and compared in order to develop accurate and useful information. One attempted solution to the inefficiency problem includes manually typing the fitness data into a computer and retaining the data as an electronic file. The procedure is still time consuming and inconvenient although the fitness data may be more easily organized and accessed once the data is in the electronic format.

Other attempted solutions include entering the fitness data directly into an electronic device such as a personal digital assistant at the time the activities or exercise is performed. This conventional technique, however, is limited in that fitness, participants must have a portable electronic device and must be willing to bring it to the fitness facility where the activities and exercises will be performed. There is risk that the portable electronic device will be lost or stolen. Due to the cost of such devices, many fitness participants prefer not to manage the fitness data in this manner.

Many pieces of exercise equipment, when utilized regularly, are very useful for weight loss, for improving cardiovascular stamina, and for strengthening various muscles. Most exercise equipment includes a monitoring device that may include a pulse monitor, a distance meter, a rate monitor, a time monitor, a strain gauge, an accelerometer and/or any other sensor for measuring the physical activity/ performance level of a user on the equipment. Moreover, monitoring devices typically request personal data from the user such as age, weight and desired physical fitness level. The monitoring device utilizes the personal data in combination with physical exertion and heart rate to estimate calories burned, fitness levels met, and other fitness related data. In addition, the monitor may adjust the resistance or speed of a piece of exercise equipment in order to aid the user in reaching and/or maintaining a fitness level for that exercise session.

One limiting factor of many exercise machines and monitors is that the user must reenter their personal data to the monitor each time the user utilizes an exercise machine. In addition, most exercise machines do not have a previous history of the user from which to provide data about improvement and to provide additional fitness goals.

Another limiting factor of many exercise machines is that they operate and monitor the user independent of one another. However, cross-training across multiple machines is popular in order to exercise different parts of the body. Moreover, another limiting factor of many exercise machines is that they are boring to utilize because of their inability to encourage a user to continue exercising. Display screens that depict a user's location within a selected exercise program may be provided; however, they typically include all graphics.

Accordingly, there is currently a need for an apparatus, system and method for managing fitness data that is efficient, inexpensive, and convenient. The present invention addresses the above described need by providing a uniquely designed system that includes a web portal for creating individual profiles and/or accounts with their biometric data, conveniently updated the user's profile with their fitness activity.

As such, it may be appreciated that there continues to be a need for a new and improved system and method as set forth by the instant invention which addresses the problems of ease of use as well as effectiveness in construction in providing an authentic electronic wellness record and in this respect, the present invention substantially fulfills this need.

SUMMARY OF THE INVENTION

In view of the foregoing disadvantages inherent in the known types of the systems and methods for maintaining the wellness or fitness records now present in the prior art, the present invention provides an apparatus, system and method for managing fitness data, wherein the same provides a technology, associated with a web portal for maintaining the fitness records and use on process of various components employed in the procedure. As such, the general purpose of the present invention, which will be described subsequently in greater detail, is to provide a new and improved system, method and device for managing the fitness data which has all the advantages of prior art and none of the disadvantages.

Accordingly, it is a primary aspect of the present invention to provide a system, method and device associated with the individual user's profile or account on a web portal.

In another aspect, the present invention, provide an improved method, system and program for monitoring exercise and managing fitness activity across diverse exercise machines with the user's profile or account.

It is yet another aspect of the present invention where the various fitness equipment are linked with the web portal system.

It is another aspect of the present invention to provide a system and/or method for generating authenticated fitness report for both, individual users and fitness center users.

In a further aspect, the biometric reading device is provided with a touch screen, front facing camera, finger print scanner, and extendable voice recorder for capturing the biometric data.

Additionally, the device is also provided with the power source input, an audio output, speakers, micro USB cable input and motion sensor input.

In another aspect, the biometric reading device is operated either by the battery source or electricity or both.

Further aspect of the present invention provides an easy and convenient method to use the system, provided with the "How to guide" handouts.

It is a still further aspect to provide an exercise monitoring analyzer to report to the user progress on his present workout performance.

It is a further aspect of the present invention to provide a user with a portable exercise monitoring personal module which contains the user's previous efforts.

Another aspect of the present invention is to provide to the user with an indication of how to change his rate of exercising to obtain the maximum benefit from the exercise routine.

It is still another aspect of the present invention to provide a new and improved system, method and device which may be easily and efficiently manufactured and marketed.

It is a further aspect of the present invention to provide a new and improved system, method and device which is of a durable and reliable construction.

Other aspects of the present invention will become apparent from time to time throughout the specification as hereinafter related.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

These together with other objects of the invention, along with the various features of novelty which characterize the invention, are pointed out with particularity in the disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

To further clarify various aspects of some example embodiments of the present invention, a more particular description of the invention will be rendered by reference to specific embodiments thereof which are illustrated in the appended drawing. It is appreciated that the drawing depicts only illustrated embodiments of the invention and are therefore not to be considered limiting of its scope. The invention will be described and explained with additional specificity and detail through the use of the accompanying drawing in which:

FIG. 5 is a front view of the biometric reading device with markings.

FIG. 6 is a side view of the biometric reading device with markings.

DETAIL DESCRIPTION OF THE INVENTION

Various aspects of the illustrative embodiments will be described using the terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

A system, method and device provide efficient, inexpensive and convenient management of fitness data. In accordance with the exemplary embodiment of the invention, fitness data is extracted from a data record and stored as electronic fitness data in a format that can be manipulated by a web portal. The electronic fitness data is accessible at a user terminal through a packet switched network such as the Internet. In the exemplary embodiment, a server or web portal stores and organizes the electronic fitness data as well as providing fitness information derived from the electronic fitness data. The fitness information may be displayed in any of several reporting formats including graphical, tabular, or textual formats. In some circumstances, additional information may be displayed with the fitness information to the user. Such information may include text, images or hypertext links for advertisements, articles, glossaries, discussion boards, message boards, statistical data, schedules, and directories related generally to fitness and wellness management.

With reference now to the drawings, and in particular to FIG. 1 to FIG. 4 thereof, a new and improved system, method and device for managing the fitness data embodying the principles and concepts of the present invention are described herein.

Figure 1:
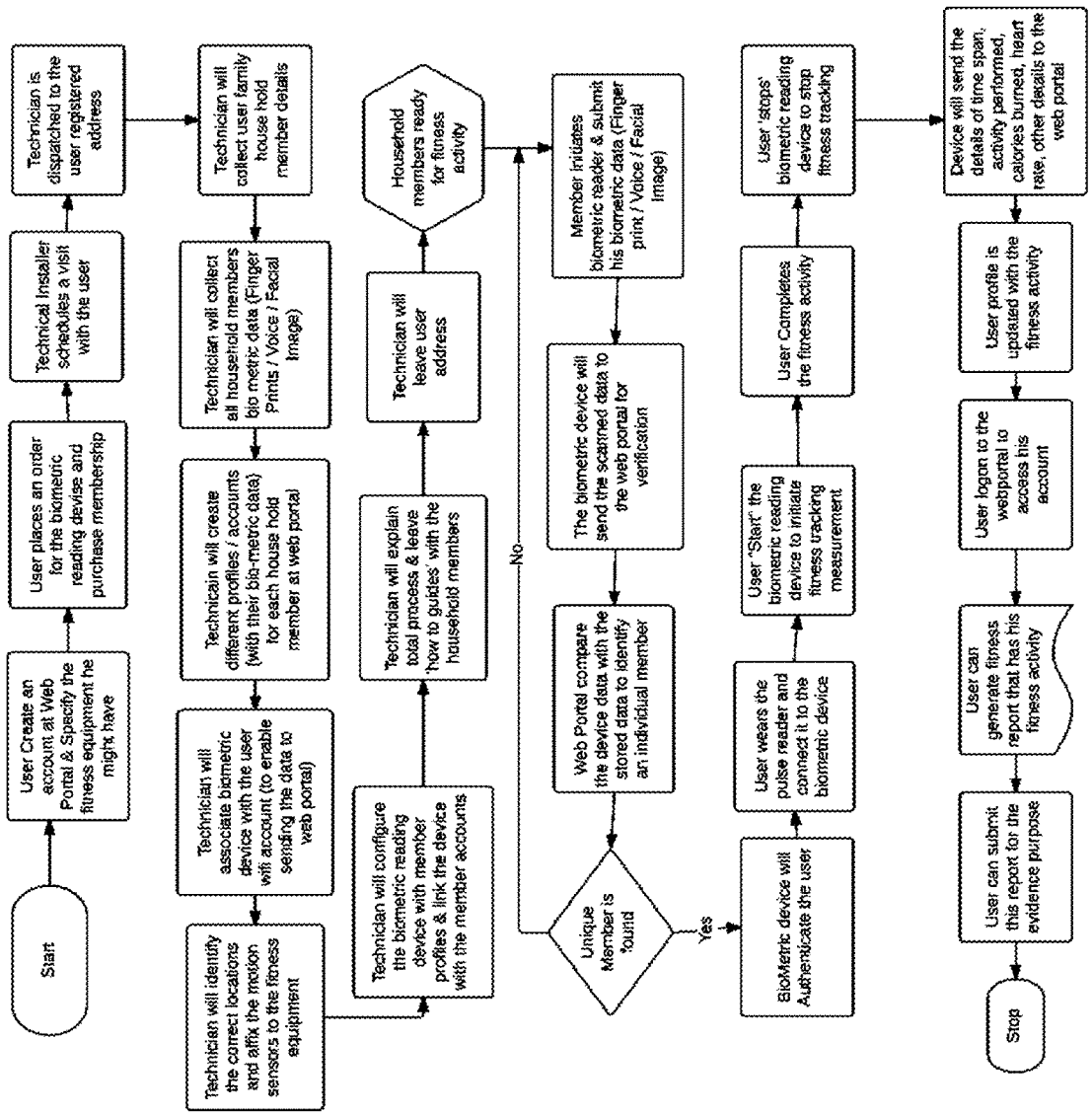
FIG. 1 is a flow chart illustrating a method for generating an authenticated fitness report for individual users.

FIG. 1 is a flow chart of a method of fitness data management in accordance with the exemplary embodiment. The method generates an authenticated fitness report for the individual user. The method may be performed using any hardware or software within in a single device or in a distributed network on web portal or system. In the exemplary embodiment, the method is performed by the fitness data management system.

As in FIG. 1, the method depicts the procedure for generating authenticated fitness report for the individual user, wherein the user creates an account at the web portal, creating their personal profile therein. Further, the user specifies the number and detail of the fitness equipment's he or she is possessing. Thereafter, user places an order for the biometric reading device and purchases the membership at the web portal.

After purchasing the membership, a technical installer would schedule a visit and will create the different profiles/accounts of all the members of the house with their respective biometric data. The biometric data includes fingerprints, voice recordings, and/or facial images. It is a responsibility of technician to configure the biometric reading device, including configuring the motion sensors by attaching the sensors at approximate location on the fitness equipment, with the individual member's profile and also to link the device with the account of each member, and handover the device to the user.

Further embodiment discloses the method for operating the device by the user after being handover by the technician. However, it is easy to use the device but for the user's convenience the device is provided with the "How to guides" handout. The first member will initiate the biometric reader and submit his biometric data (fingerprint, voice recording and facial image). The device will send the scanned biometric data to the web portal for verification. The device data is then compared with the stored data at the web portal to identify an individual. The different profiles/account would be created for each member of the house.

In accordance with the above disclosed method, if a unique member is being found the biometric device will authenticate the user and initiate their fitness tracker to perform the fitness activity. Just before starting the fitness activity, the user will wear the pulse tracker and attach it to the biometric devise and initiate the fitness activity. After completing the fitness activity, the user will stop the tracker and the device will send the fitness tracking details such as time span, activity performed, calories burned, heart rate, and the like details to the web portal. The data is thus saved to the web portal linked with each profile or account and is accessible on further logging on the web portal. In this way, the user is able to keep the record of his present fitness activity and the web portal will maintain the data for future correspondence and also user can compare the present activity record with their own past records.

In further embodiment, if the unique member is not found by the web portal, while verifying the provided biometric data with the stored data, the overall process will be repeated, from initiating the biometric reader till sending the data to the web portal.

Figure 2:
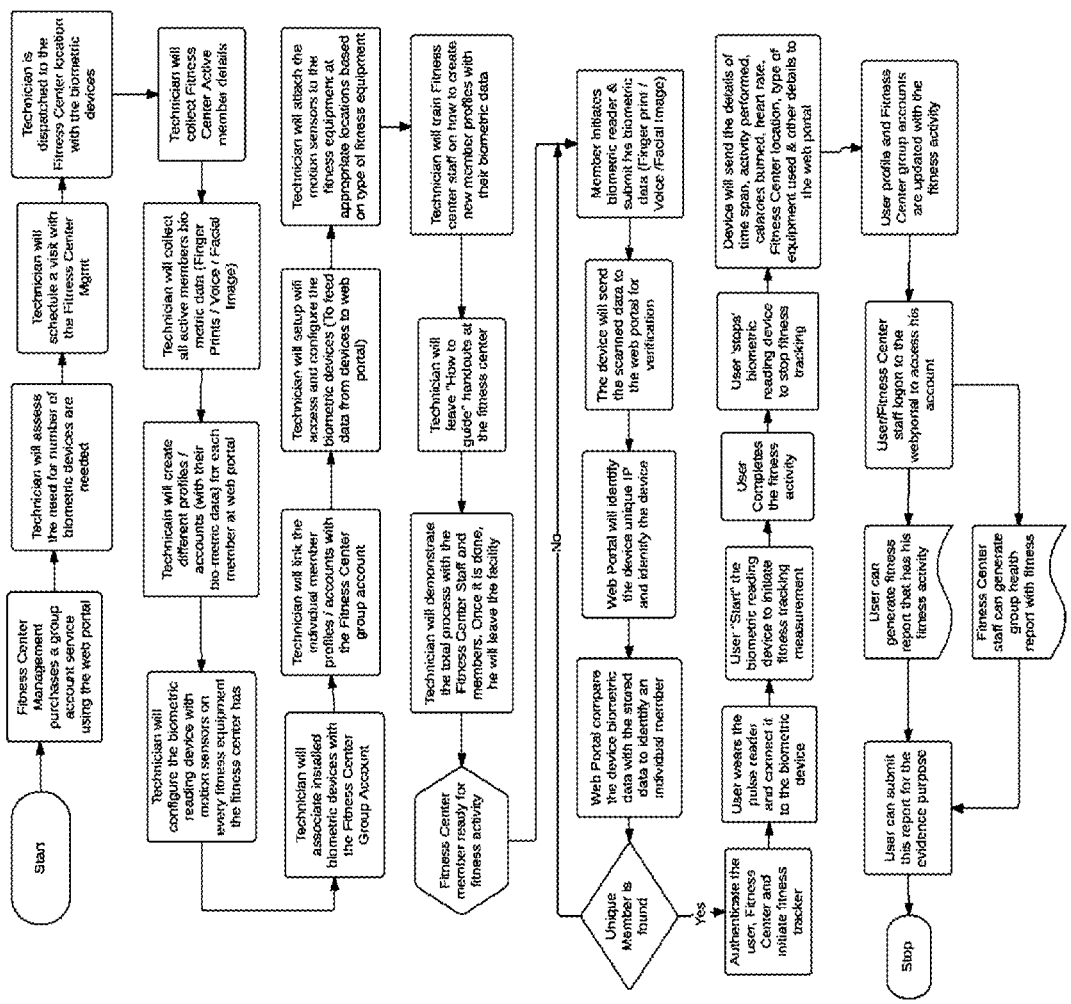
FIG. 2 is a flow chart illustrating a method for generating an authenticated fitness report for fitness center users.

In another preferred embodiment of the present invention, where FIG. 2 discloses the procedure for generating authenticated fitness report for the fitness center user, via flow chart method. The method is similar to the method described above with the flow chart in FIG. 1.

Firstly, the fitness center management purchases a group account service using the web portal, defining the number of biometric reading devices needed for the fitness center. The technician is communicated to schedule a visit for the fitness center with the required biometric reading devices. Further, it is the technician's responsibility to collect all active members' biometric data, viz. Finger prints, voice recordings, facial images, and creating the profile or account, with their respective biometric data, for each member at the web portal. The biometric reading devices are to be configured, by the technician on all fitness equipment of the fitness center and linked to the fitness center group account. The technician is responsible to identify the motion sensor locations and attaching the sensors on the fitness equipment appropriately. A Wi-Fi access is set up to feed the data from the biometric reading devices to the web portal.

The technician will also train the fitness center staff, the procedure for creating the new member profiles with their biometric data, providing "How to guide" handouts to the fitness center staff, and demonstrating the overall process for using the biometric reading device and transferring the biometric data to the web portal.

The fitness center staff will assist the members of that fitness center in recording and managing their individual fitness track records. Each member then initiates the biometric reader and submits his/her biometric data, which is further scanned by the biometric reading device and send to the web portal for the verification. The web portal will identify the device unique IP and compare the device biometric data with the stored data to identify an individual member.

Similarly, as described above in flow chart 1 (FIG. 1), if the unique member is found by the web portal, biometric device will authenticate the user and initiate their fitness tracker to perform the fitness activity. And if the unique member is not found, the process has to be repeated. Briefly, the steps to be followed by the member of the fitness center to maintain their fitness activities are as follows:

a) The user first initiates the fitness tracker by pressing start button on the biometric reading device. The user also wear the pulse reader and attach the pulse reader to the biometric device.
b) The user will perform and complete his fitness activity.
c) User will stop the biometric reading device to stop fitness tracking.
d) Device will send the details of time span, activity performed, calories burned, heart rate, type of equipment used, and location of fitness center and other like details to the web portal.
e) User's profile and fitness center group accounts are updated with the fitness activity.
f) Both user and fitness center staff can logon to the web portal to access the user's account to generate the fitness report of the respective user. The fitness center staff can also generate the group health report.
g) User will then submit this report for evidence purpose.

Figure 3:
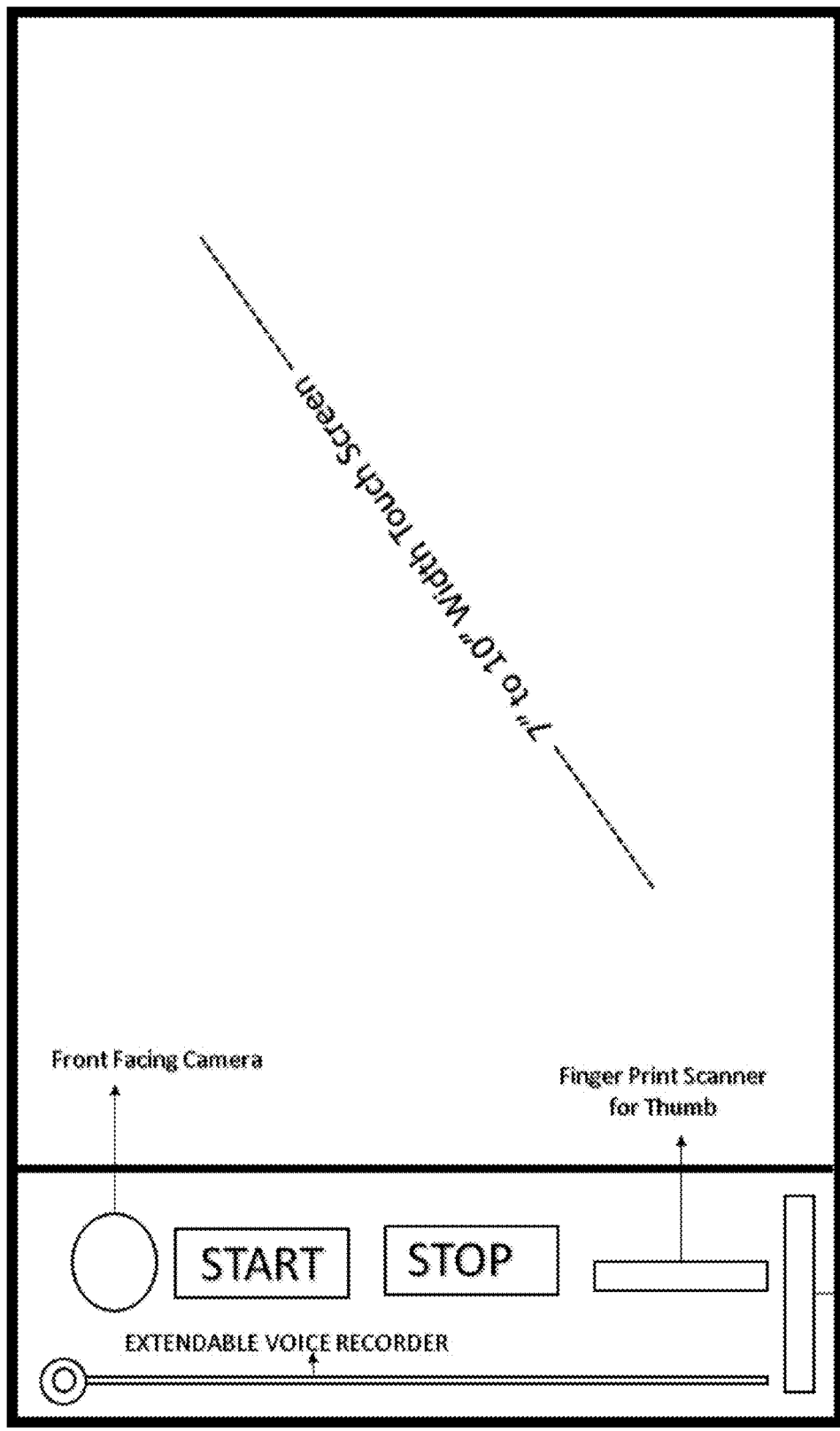
FIG. 3 is a front view of the biometric reading device.

Further embodiment discloses the biometric reading device with the help of the FIG. 3, front view of the biometric reading device is described herein. The device is approximately 7 inches in size and weight around 10 oz. The device comprises 7"-10" wide touch screen with the front camera, finger print scanner for thumb, finger print scanner for index finger, and extendable voice recorder at the base panel. The biometric reading device also involves the circuit board, essential to be linked with the web portal.

The biometric reading device also includes the 'Start' and 'Stop' press button to initiate and stop the fitness tracking record respectively.

Figure 4:
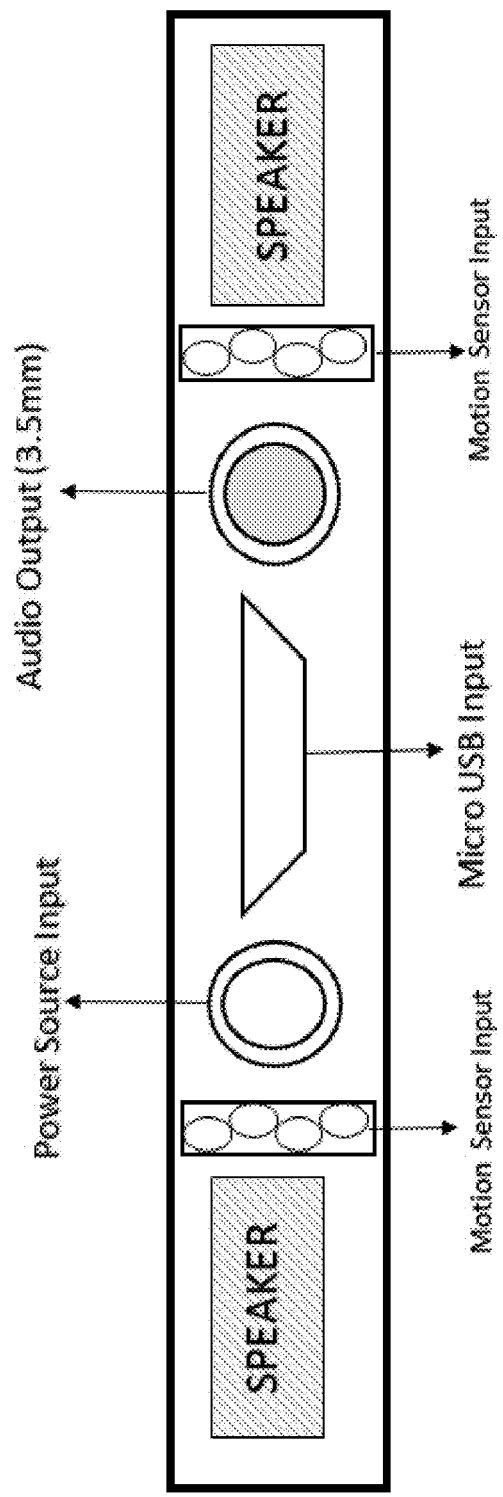
FIG. 4 is a side view of the biometric reading device.

Turning to the FIG. 4, side view of the biometric reading device discloses the another embodiment of the present invention, wherein the device involves the speakers at both ends, motion sensors adjacent to both the speakers, audio output (3.5 mm) and the micro USB cable input. The biometric reading device also comprises the power source input, whereby the device may be operated by battery source or electricity or both.

It is to be understood that the above description is intended to be illustrative, and not restrictive. For example, the above-discussed embodiments may be used in combination with each other. Many other embodiments will be apparent to those of skill in the art upon reviewing the above description.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A method for generating an authenticated wellness activity report for an individual user with a biometric device comprising a touch screen unit with a display, a front camera, first finger print scanner, second finger print scanner, and extendable voice recorder, a start press button and a separate stop press button to start and stop tracking wellness activity data respectively, two separate speakers located at a side panel of the unit, two separate motion sensor inputs, located at the side panel of the unit, an audio output, a micro USB input, and a power input located at the side panel of the unit, and an integrated circuit board with processor and network card, the steps comprising:
  a) connecting the power input of the biometric device to a power supply,
  b) accessing the internet via the network card,
  c) creating an individual user account profile comprising user information including biometric data obtained from the at least one finger print scanner, voice recorder, and camera,
  d) updating the user profile with user fitness equipment,
  e) connecting the biometric device with user equipment via the micro-USB,
  f) configuring motion sensors, connected to the motion sensor inputs of the biometric device, with the user equipment,
  g) sensing a user's biometric data with the biometric device,
  h) authenticating the user based on the sensed biometric data,
  i) recording the user's wellness activity data with the biometric device start and stop buttons respectively, including at least calories burned, duration of wellness activity, fitness equipment used, heart rate, and blood pressure,
  j) updating the user profile with the recorded wellness activity data, and
  k) generating the user's wellness activity report, comprising at least the wellness activity data.

2. A method for generating an authenticated wellness activity report for a commercial user with a biometric device comprising a touch screen unit with a display, a front camera, first finger print scanner, second finger print scanner, and extendable voice recorder, a start press button and a separate stop press button to start and stop fitness tracking wellness activity data respectively, two separate speakers located at a side panel of the unit, two separate motion sensor inputs, located at the side panel of the unit, an audio output, a micro USB input, and a power input located at the side panel of the unit, and an integrated circuit board with processor and network card, the steps comprising:
  a) connecting the power input of the biometric device to a power supply,
  b) accessing the internet via the network card,
  c) creating active user profiles comprising user information including biometric data obtained from the at least one finger print scanner, voice recorder, and camera,
  d) connecting the biometric device to fitness center equipment or user equipment via the micro-USB,
  e) configuring motion sensors connected to the motion sensor inputs of the biometric device with the fitness center equipment or user equipment,
  f) sensing a user's biometric data with the biometric device,
  g) authenticating the user based on the sensed biometric data,
  h) recording the user's wellness activity data with the biometric device start and stop buttons respectively, including at least calories burned, duration of wellness activity, fitness equipment used, heart rate, and blood pressure,
  i) updating the user profile with the recorded wellness activity data, and
  j) generating the wellness activity report, comprising at least the wellness activity data, based on an individual account or a group account.

* * * * *